United States Patent
Moon et al.

(10) Patent No.: US 10,188,098 B2
(45) Date of Patent: Jan. 29, 2019

(54) EXTREMELY FAST FREEZING, LOW-TEMPERATURE BLAST FREEZER

(71) Applicants: William G. Moon, Provo, UT (US); William J. Hancock, Bellevue, WA (US); Steven V. Boyce, Spanish Fork, UT (US); Steven J. Parkinson, Clinton, UT (US)

(72) Inventors: William G. Moon, Provo, UT (US); William J. Hancock, Bellevue, WA (US); Steven V. Boyce, Spanish Fork, UT (US); Steven J. Parkinson, Clinton, UT (US)

(73) Assignee: Reflect Scientific Inc., Orem, UT (US)

( * ) Notice: Subject to any disclaimer, the term of this patent is extended or adjusted under 35 U.S.C. 154(b) by 24 days.

(21) Appl. No.: 15/296,009

(22) Filed: Oct. 17, 2016

(65) Prior Publication Data

US 2017/0234597 A1    Aug. 17, 2017

Related U.S. Application Data

(63) Continuation-in-part of application No. 12/464,701, filed on May 12, 2009, now abandoned, and a continuation-in-part of application No. 12/574,670, filed on Oct. 6, 2009, now Pat. No. 8,448,454.

(51) Int. Cl.
| | |
|---|---|
| *F25D 3/02* | (2006.01) |
| *A01N 1/02* | (2006.01) |
| *F25D 3/10* | (2006.01) |
| *F25D 17/06* | (2006.01) |
| *F25D 29/00* | (2006.01) |

(52) U.S. Cl.
CPC .......... *A01N 1/0257* (2013.01); *F25D 3/102* (2013.01); *F25D 17/06* (2013.01); *F25D 29/001* (2013.01); *F25D 29/006* (2013.01); *F25D 2700/122* (2013.01)

(58) Field of Classification Search
CPC ............................... A01N 1/0284; F25D 3/11
USPC .......................................................... 62/50.2
See application file for complete search history.

(56) References Cited

U.S. PATENT DOCUMENTS

| | | | | |
|---|---|---|---|---|
| 3,678,716 | A * | 7/1972 | Cobb ................. | E05B 65/0053 292/179 |
| 4,138,049 | A * | 2/1979 | McAlarney .......... | F25D 23/087 277/629 |
| 4,436,692 | A * | 3/1984 | Stenabaugh ....... | G21C 13/0285 376/204 |
| 4,741,172 | A * | 5/1988 | Aoki ........................ | A47F 3/00 62/248 |
| 4,986,086 | A * | 1/1991 | de Langavant ...... | B60H 1/3202 62/208 |

(Continued)

*Primary Examiner* — Henry Crenshaw
(74) *Attorney, Agent, or Firm* — Tran & Associates

(57) ABSTRACT

A freezer includes a plurality of shelves in an insulated payload bay; a plurality of evaporators coupled to the payload bay with a multiplicity of coolant tubes in each evaporator, wherein each tube enters and then exits the payload bay, further comprising one or more cryogenic valves coupled to the coolant tubes; a pump to force coolant flowing through the evaporators with a pressure of at least 90 psi to supply the coolant at each evaporator with at least 20 gallons per hour of coolant; and a plurality of fans to circulate cooled air in the payload bay.

16 Claims, 7 Drawing Sheets

(56) References Cited

U.S. PATENT DOCUMENTS

| | | | | |
|---|---|---|---|---|
| 5,163,301 A * | 11/1992 | Cahill-O'Brien | ..... | F25B 41/043 236/78 C |
| 5,186,008 A * | 2/1993 | Appolonia | ............. | A23L 3/363 62/266 |
| 5,267,443 A * | 12/1993 | Roehrich | ............. | B60H 1/3202 62/167 |
| 5,484,204 A * | 1/1996 | Damley | ................ | F25D 19/006 374/10 |
| 5,568,800 A * | 10/1996 | Einaudi | ................. | F02M 17/16 123/546 |
| 5,660,046 A * | 8/1997 | de Langavant | ......... | F25D 3/105 62/239 |
| 2002/0000092 A1* | 1/2002 | Sharood | ................. | F25D 29/00 62/127 |
| 2003/0033825 A1* | 2/2003 | Goosman | ................ | B60H 1/3232 62/239 |
| 2003/0051486 A1* | 3/2003 | Ursan | .................... | F04B 15/08 62/50.6 |
| 2003/0086338 A1* | 5/2003 | Sastry | ................ | G06F 19/3462 368/10 |
| 2003/0089493 A1* | 5/2003 | Takano | ................ | B60H 1/00914 165/202 |
| 2003/0091347 A1* | 5/2003 | Goto | ................. | G03C 1/49881 396/564 |
| 2003/0221726 A1* | 12/2003 | Semeia | ............... | B63C 11/2209 137/338 |
| 2004/0089012 A1* | 5/2004 | Chen | ........................ | F25B 9/14 62/277 |
| 2004/0104654 A1* | 6/2004 | Lee | ........................ | F25D 21/04 312/401 |
| 2005/0070848 A1* | 3/2005 | Kim | .................... | A61M 5/2053 604/140 |
| 2005/0126630 A1* | 6/2005 | Swan | ........................ | E03B 7/12 137/80 |
| 2005/0178285 A1* | 8/2005 | Beers | ........................ | B60P 3/20 105/404 |
| 2006/0202042 A1* | 9/2006 | Chu | .................... | G06K 17/0022 235/492 |
| 2007/0157645 A1* | 7/2007 | Anell | .................... | F25D 17/065 62/187 |
| 2009/0229282 A1* | 9/2009 | Taras | ..................... | F25B 39/02 62/117 |
| 2013/0247605 A1* | 9/2013 | Laudet | ............... | B60H 1/00378 62/239 |
| 2015/0330679 A1* | 11/2015 | Bowdish | ............ | B60H 1/00014 62/239 |
| 2015/0343881 A1* | 12/2015 | Farrington | ........... | B60H 1/3233 62/121 |

\* cited by examiner

EXTREMELY FAST FREEZING, LOW-TEMPERATURE BLAST FREEZER

FIELD OF INVENTION

The present invention relates to high speed cooling freezers.

BACKGROUND OF THE INVENTION

Many applications require the specific capability of freezing a product in an extremely short time. Exemplary users include companies that require plasma or blood related products to be frozen quickly and completely to −40 C. Such companies contain their product in a multiplicity of specially formulated plastic bags that contain between 250 cc and 500 cc of plasma or blood related products. These companies may freeze up to 100 bags simultaneously, placing approximately 10 bags on a tray and up to 10 trays in the freezer. Traditionally, cooling devices known in the industry as Blast Freezers are used with the unique capability of freezing the customer's products at a substantially faster rate than standard laboratory or storage freezers.

Typically, state of the art Blast Freezers are mechanical, with compressors and refrigerants. The main drawback is that the boiling point of the refrigerant is approximately −100 C which severely limits the ability to freeze product quickly. As an example, these freezers are unable to freeze a batch of 100 bags to −40 C in less than 2 hours.

SUMMARY

In one aspect, a freezer includes a plurality of shelves in an insulated payload bay; a plurality of evaporators coupled to the payload bay with a multiplicity of coolant tubes in each evaporator, wherein each tube enters and then exits the payload bay, further comprising one or more cryogenic valves coupled to the coolant tubes; a pump to force coolant flowing through the evaporators with a pressure of at least 90 psi to supply the coolant at each evaporator with at least 20 gallons per hour of coolant; and a plurality of fans to circulate cooled air in the payload bay.

In another aspect, a freezer includes 1 a liquid Nitrogen inlet capable of convenient attachment to a customer's liquid Nitrogen supply;
2 a cryogenic flow system that operates at a predetermined Nitrogen flow;
3 a payload bay with removable shelves;
4 a plurality of evaporators inside the payload bay.
5 A plurality of fans that distribute the cooled air from the evaporators to the payload bay.
6 a fan and evaporator support structure with a multiplicity of holes that selectively direct the cooled airflow to provide even cooling throughout the payload bay.
7 a thermal box immediately outside the evaporators and payload bay, that effectively thermally seals the payload bay from the outside environment, significantly reducing heat gain;
8 an electronic controller that maintains a setpoint for the payload bay, determined by the operator between approximately 20 degree C. and −150 degree C.;
9 a pneumatic latch that secures the freezer;
10 a pneumatic rubber seal that provides an airtight seal for the payload bay; and
11 electronics and mechanics that controls payload bay temperatures consistently within +/−3 degree C. of the setpoint throughout the shipment duration.

In another aspect, a freezer system is designed for freezing a customer's product at an extremely fast rate compared to prior art products, to temperatures as low as −150 C. The freezer is comprised of a large payload bay, an inlet for the customer's supply of a cryogenic liquid such as Nitrogen, evaporators inside the payload bay, and a plurality of fans adjacent to the evaporators, that deliver extremely cold air to all surfaces of the customer's product for fast convective cooling. Further, the temperature is controlled at the exhaust port of the freezer with a cryogenic solenoid valve.

Advantages of the system may include one or more of the following. The preferred embodiment has the capability of reducing the freeze time of about 100 bags to about 1 hour, which is one-half the time of conventional freezers. Further, the payload bay has 20 shelves and is capable of freezing 200 bags in one batch. These almost unheard of freezing times are accomplished by design: 1) The coolant is Liquid Nitrogen, having a boiling point of −196 C, almost 100 C colder than the refrigerants used in mechanical freezers; 2) The supply pressure of the Liquid Nitrogen coolant is approximately 100 psi, which is much higher than conventional Nitrogen freezers, thus significantly increasing the coolant flow; and 3) The convective cooling properties of the freezer are greatly enhanced through the addition of a plurality of fans inside the payload bay.

DESCRIPTION

A detailed description of the preferred embodiment is provided herein. It is to be understood, however, that the present invention may be embodied in various forms. Therefore, specific details disclosed herein are not to be interpreted as limiting, but rather as a basis for the claims and as a representative basis for teaching one skilled in the art how to employ the present invention in virtually any appropriately detailed system.

Figure 1:
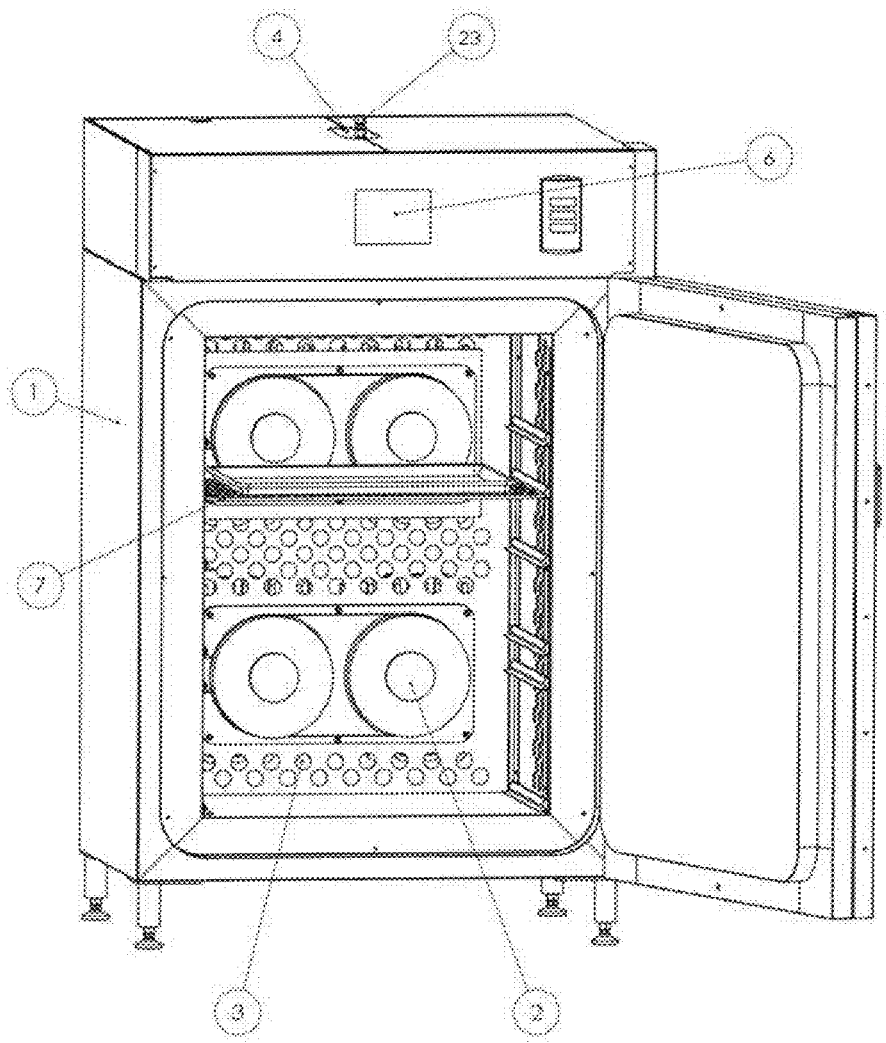
FIG. 1 is an exemplary 3D perspective view of the front of a Blast Freezer.
Figure 2:
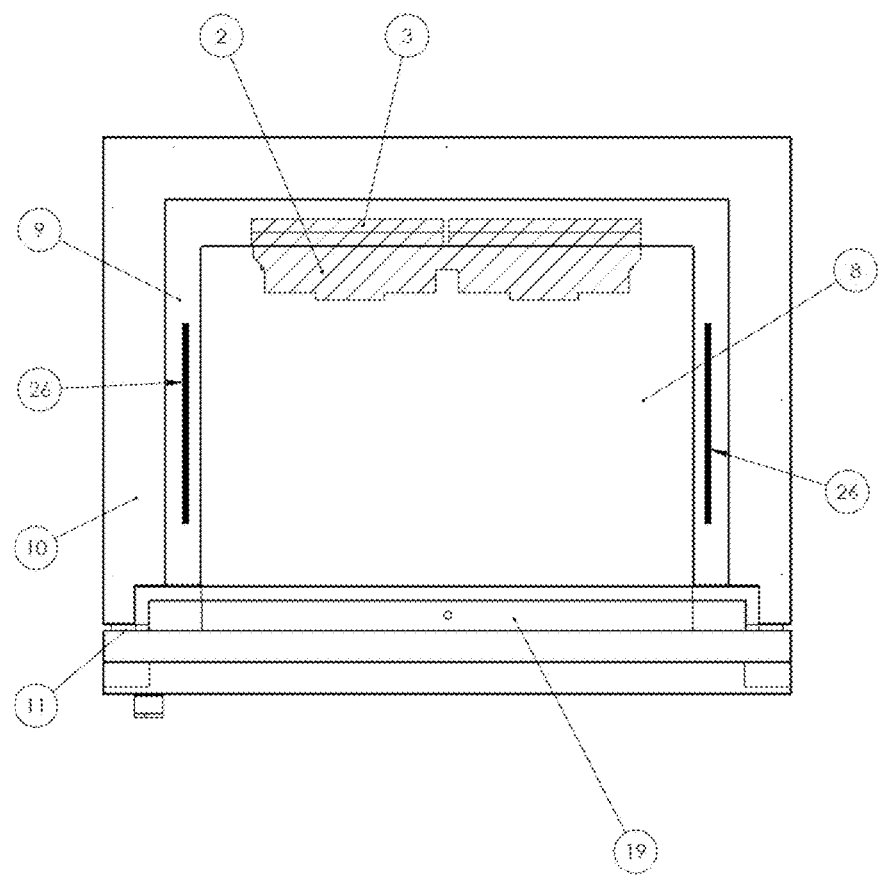
FIG. 2 is an exemplary top view of the Blast Freezer.
Figure 3:
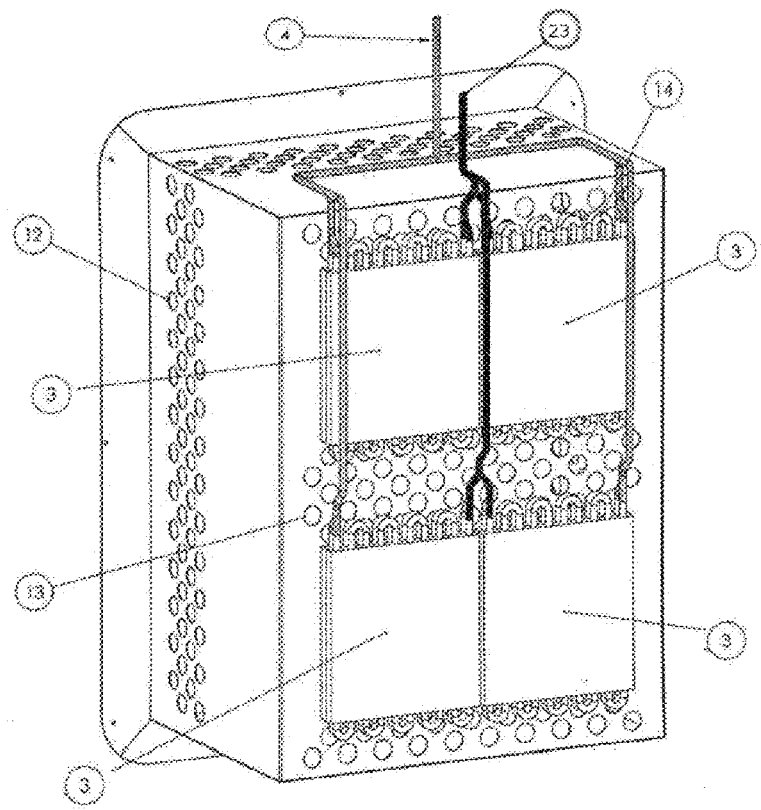
FIG. 3 is an exemplary 3D view of the back inside of the Blast Freezer.
Figure 4:
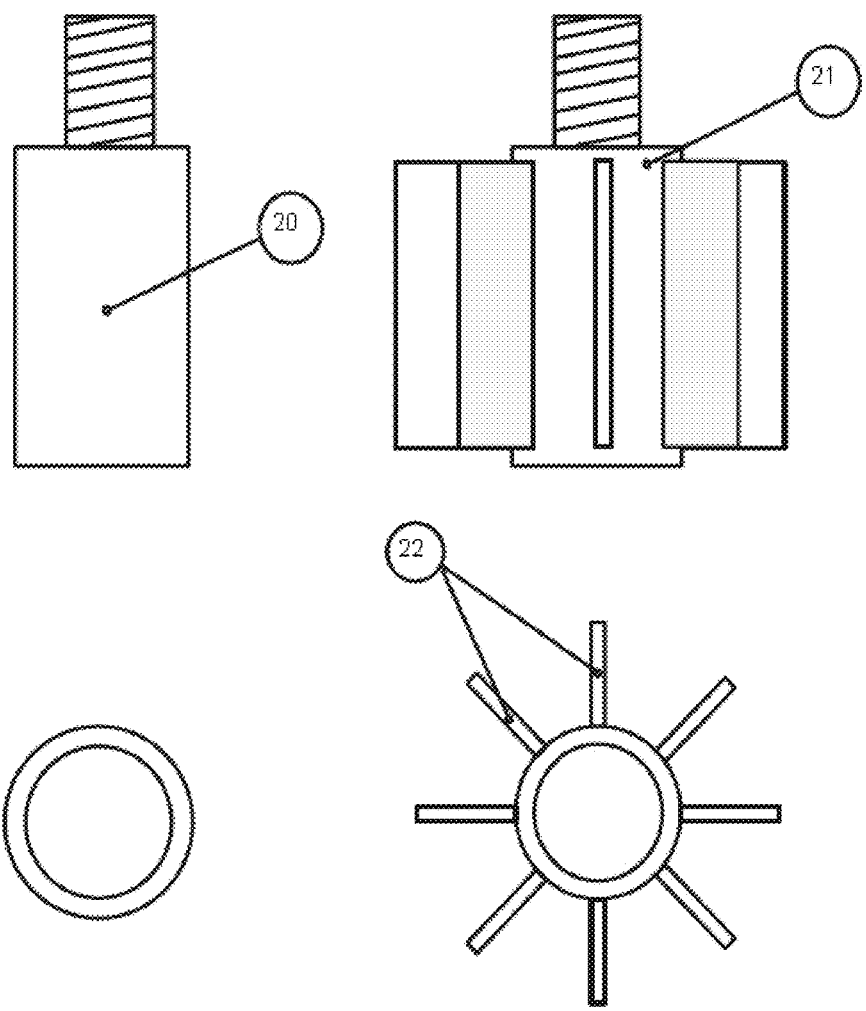
FIG. 4 is an exemplary drawing of the safety valve heating fins.
Figure 5:
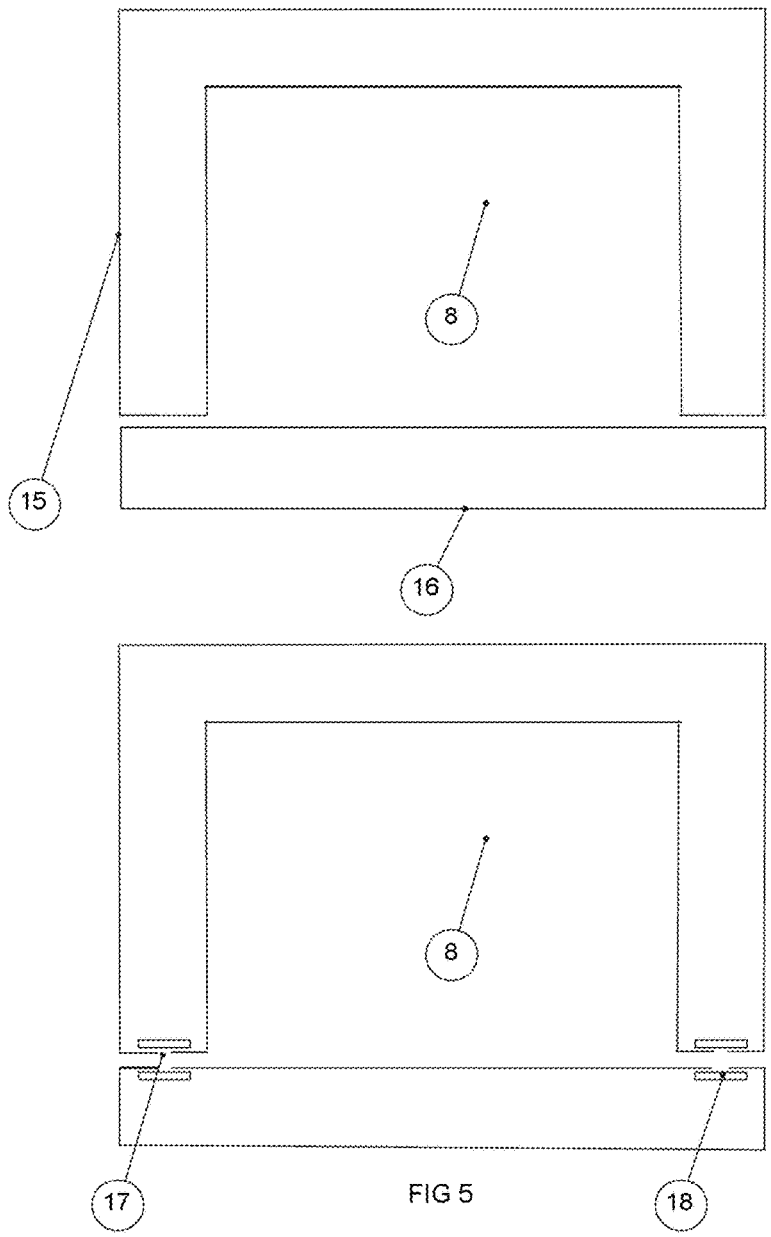
FIG. 5 is an exemplary cross section top view of the thermal barrier.

Now referring to FIGS. 1 through 3, the preferred embodiment is a freezer system 1 with a plurality of shelves 7, connected to a coolant such as a liquid Nitrogen source, and set to a pressure of 100 psi, for example. In contrast, conventional liquid Nitrogen freezers are typically set to 35 psi. The preferred embodiment, with 3 times the pressure, will supply coolant at up to 9 times the flow of conventional freezers. The 100 psi pressure will cause flows as high as 30 gallons per hour of liquid Nitrogen, thus providing extremely fast cooling. In one embodiment, a pump is used to force coolant flowing through the evaporators with a pressure of at least 90 psi to supply the coolant at each evaporator with at least 20 gallons per hour of coolant. The Nitrogen source is attached to the freezer 1 with a standard CGA 295 fitting 4. The coolant flows to a plurality of evaporators 3 that have a multiplicity of copper tubes 14 in each evaporator, thus maximizing the transfer of heat from the Liquid Nitrogen to the payload bay 8. The copper tube then exits the payload bay, where the cryogenic fluid is controlled with a cryogenic solenoid valve 5. The exhaust port 23 is then attached to a customer portal that provides a pathway for the Nitrogen gas to flow outside the building.

As a means of significantly improving the freezing rate, multiple fans 2 with typical airflows of 1,000 CFM rapidly distribute air around the customer's containers, thus increasing the cooling convection properties of the freezer. Also, vent holes 12 and 13 are strategically placed as a means of ensuring uniform temperature throughout the payload bay.

A separate compartment 10, located between the payload bay and the outside environment, of between 2 and 4 inches thick contains a plurality of insulation materials that substantially reduces the heat gain of the payload bay from the environment.

A thermocouple, inside the payload bay, measures the temperature at all times and sends a signal to the controller 6, where it is carefully monitored and the temperature is controlled. When the setpoint is reached, the controller 6 will stop the flow of liquid Nitrogen through the evaporators 3 by turning the cryogenic solenoid valve 5 off. The cryogenic solenoid valve 5 controls the Nitrogen flow in a location that is considered unique by those familiar with the state of the art.

Typically, the solenoid valve 5 is located in the coolant path between the source and the freezer 1. Said valve 5 is located at the exhaust port 23 of the freezer, which provides equivalent control, but provides a substantially warmer environment for the valve, thus increasing the reliability and life of the valve.

The controller 6 monitors the payload bay temperature via a thermocouple and will use algorithms familiar to those skilled in the art of feedback control systems, such as PID control, to maintain the setpoint within a reasonable limit, such as +/−3 C in the preferred embodiment.

A further advantage of the system is the capability of cooling the room where the freezer is located. All mechanical freezers accomplish cooling by transferring heat from the payload bay to the surrounding environment, thus heating the room. Typically, a room with several mechanical freezers requires a significant air conditioning system to make the room bearable for employees, and to prolong the life of other instruments and equipment in the room. However, in the preferred embodiment, the exhausting Nitrogen is typically of a sufficiently cold temperature, approximately −100 C, that it is an excellent source for providing the equivalent of an air conditioner for the room. The Nitrogen gas flows through a multiplicity of copper tubes 14 within the blast freezer 1 then through a heat exchanger 25 located on the top of the blast freezer 1. The heat exchanger 25 is similar to an air conditioner evaporator coil. The Nitrogen gas flows from the solenoid control valve through tubes 14 through heat exchanger 25, through a heat exchanger similar to an air conditioner evaporator coil, located on the top of the freezer. A fan 24 forces air through said heat exchanger 25, where the air is cooled and delivered to the room Another advantage of the Blast Freezer is the capability of heating the payload bay. Electrical heating pads 26, such as Silicone rubber heaters are located in the air flow path 9. When the customer sets the controller 6 to a temperature that is warmer than the current payload bay temperature, the heating pads are energized and continue to heat until the desired setpoint is reached.

A further advantage of the Blast Freezer is the improvement in efficiency of cooling compared to other Nitrogen freezers. Conventionally, the stainless steel walls 15 of the freezer body and door 16 are a conductive thermal path for environmental heat to pass through the exterior walls and into the payload bay 8. This problem is referred to as a "thermal short" by those skilled in the art of thermodynamics. The preferred embodiment, however, decreases the Nitrogen usage rate by as much as 30%. To eliminate this heat gain, a thermal barrier or disconnect decouples the sheet metal. The thermal barrier is a gap 17 in the sheet metal approximately ¼ inch wide in the preferred embodiment, eliminating the metal conductive thermal path. A non-metal material 18, such as a glass-based epoxy resin laminate, attached to both sides of the gap 17, provides structural support.

Typically, there is also significant heat gain through the gasket between the door and the freezer. As a means to reduce said heat gain, a rubber pneumatic seal 11 is placed between the door 16 and the payload bay 8. Said seal 11 is controlled by valve 28 and inflated from the Nitrogen gas that is readily available at all times, since it is a by product of the cooling process. A further reduction in heat gain is accomplished with an additional impediment to the heat flow by adding a second door 19 interior to the door 16.

A feature of the Blast Freezer is a means of operating the cooling system in event of power loss. Deep cycle batteries provide immediate backup energy. Further, in the event of prolonged power loss for several days, a mechanical valve 27 located in parallel with the cryogenic solenoid valve 5 provides a means for the operator to manually regulate the freezer temperature.

A safety valve 20 is used to prevent excessive pressures in the system. Said valve 20 is generally used in the industry for this type of application. However, a common problem with the safety valve 20 is that the extremely cold temperature of the liquid Nitrogen flowing through the safety valve 20 can cause the safety valve 20 to stick and remain open, when it should have closed. Further, this flow causes safety valve 20 temperature to plummet, which substantially increases the potential for a runaway condition, keeping safety valve 20 open continuously and needlessly, wasting large amounts of Nitrogen. This failure is known in the industry as "sticky valve".

To reduce this problem, heating fins 22 are added to the newly designed safety valve 21 in the preferred embodiment. These heating fins 22 keep the temperature of the valve 21 warmer during pressure relief, thus significantly reducing the sticky valve problem.

As a further means of improving reliability the preferred embodiment has no refrigeration compressor, common to most prior art freezers, thus alleviating wear problems associated with the multiplicity of moving parts. To increase reliability, mechanical valve 27 is used in parallel with cryogenic solenoid valve 5 as a backup control.

In one embodiment, a Blast Freezer 1 system includes a liquid Nitrogen inlet capable of convenient attachment to a customer's liquid Nitrogen supply and a cryogenic flow system that operates at significantly higher Nitrogen flow than conventional freezers. The system includes a payload bay 8 with removable shelves 7, a plurality of evaporators 3 inside the payload bay 8; and a plurality of fans 2 that distribute the cooled air from the evaporators 3 to the payload bay 8. A fan 2 and an evaporator support structure have a multiplicity of holes 12&13 that selectively direct the cooled airflow to provide even cooling throughout the payload bay 8. A thermal box 10 is provided immediately outside the evaporators 3 and payload bay 8 that effectively thermally seals the payload bay 8 from the outside environment, significantly reducing heat gain. The system includes a pneumatic latch 29 that secures the blast freezer 1 and a rubber pneumatic seal 11 that provides an airtight seal for the payload bay 8. An electronic controller 6 is provided that maintains a set point for the payload bay 8, determined by the operator between 20 C and −150 C. The electronics control payload bay temperatures consistently within +/−3 C of the set point throughout the shipment duration.

Figure 6:
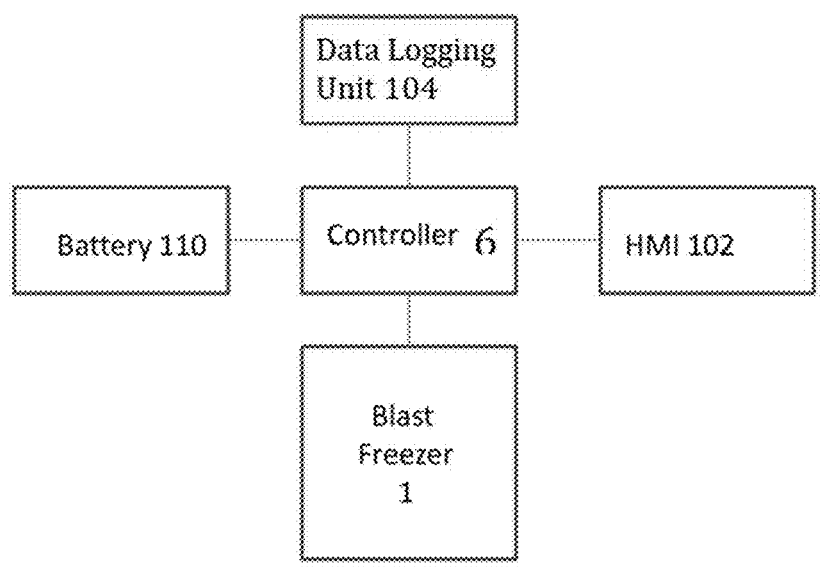
FIG. 6 shows an exemplary controller with battery backup system for the Blast Freezer.
Figure 7:
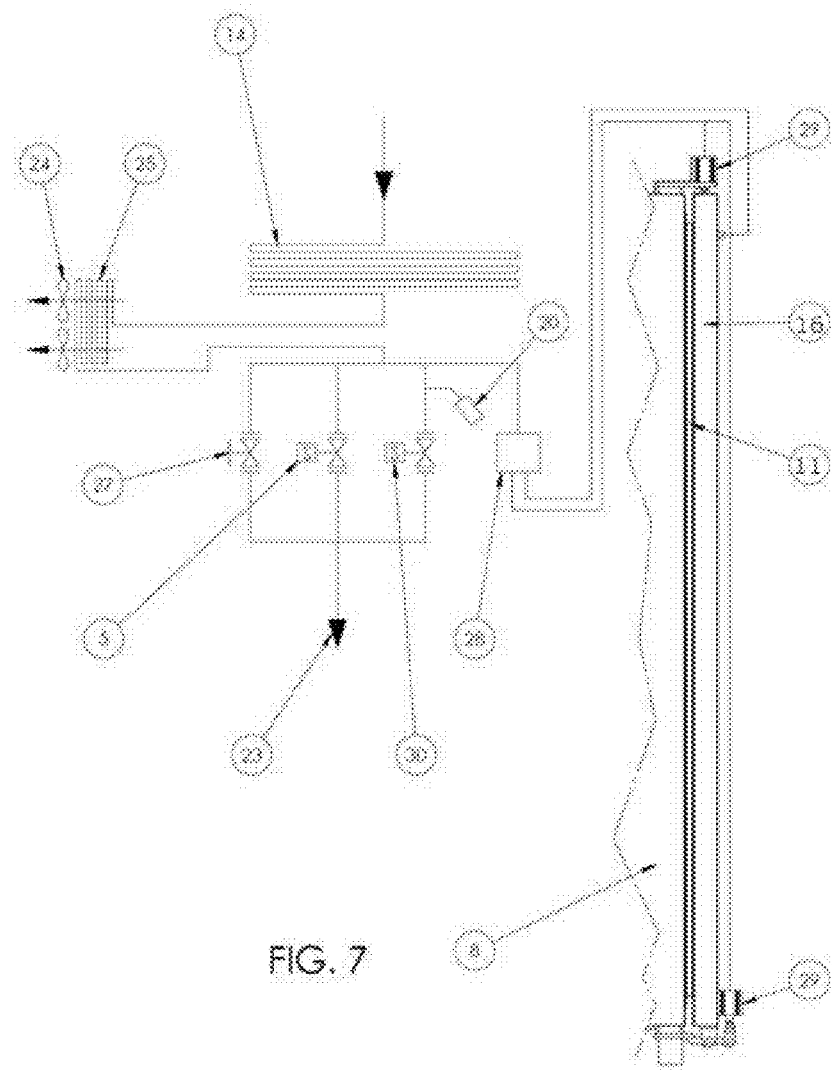
FIG. 7 shows a diagram of redundancy operations in the shipping unit.

FIG. 6 shows an exemplary blast freezer 1 with a controller 6 and a battery back-up unit 110 The controller 6 includes an interactive Human Machine Interface or HMI 102. The HMI 102 has a touch screen display. Said electronics also includes a data logging unit 104 with real time data, plotted on the display and recording temperature vs time. The electronics also includes the capability to transmit data logging information. The payload bay temperature control is provided by a cryogenic solenoid valve 5 that is precisely controlled by the electronics. Further, said temperature control is achieved through the use of PID or another algorithm known to those skilled in the art. Deep cycle batteries in the battery back-up unit 110 can provide uninterrupted power in the event of AC power loss. Additional customer product thermal safety is provided by an emergency mechanical valve 27 that regulates freezer temperature. A pneumatic latch 29 and pneumatic rubber seal 11 can be used and can be powered by the pressure derived from the Nitrogen exhaust gas. The newly developed safety valve 21 has a mechanism to prevent a failure known in the industry as a "sticky valve", through the attachment of heating fins 22 to the outside diameter. The assembly has a net thermal effect of reducing the temperature of the surrounding environment, rather than increasing the temperature, which occurs with prior art mechanical freezers. The cryogenic solenoid valve 5 is placed in the exhaust path of the Nitrogen gas. Said location provides a warmer temperature location and promotes longer valve operating life than the standard colder location that is on the substantially colder incoming side of the freezer. The system is emission free and contains no polluting refrigerants such as CFCs or HCFCs. The entire cooling system is highly reliable due to almost no moving parts. The system has the capability of heating the payload bay 8. The entire Nitrogen flow is a closed system and the liquid Nitrogen and the Nitrogen gas never come in direct contact with the customer's product or the employees.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

The invention claimed is:

1. A freezer, comprising:
 a plurality of shelves in an insulated payload bay;
 a plurality of evaporators coupled to the payload bay with a parallel array of coolant tubes in each evaporator, further comprising one or more cryogenic valves coupled to the coolant tubes, wherein one of the cryogenic valves is located at an exhaust port of the freezer;
 a rubber pneumatic seal placed between a freezer door and the payload bay;
 a pneumatic latch for latching the freezer door and the pneumatic rubber seal are powered by the pressure derived from an exhaust gas;
 a pump to force a cryogenic coolant flowing through the evaporators with a pressure of at least 90 psi to supply the coolant at each evaporator with at least 20 gallons per hour of coolant;
 a plurality of fans to circulate cooled air in the payload bay;
 a room heat exchanger valve controlling a flow of cryogen to a room heat exchanger after the cryogen exits from the evaporators, a room fan that forces air through said room heat exchanger, where the air is cooled and delivered to a room, wherein the fan is controlled by a controller with a room thermocouple as a feedback loop.

2. The freezer of claim 1, wherein the coolant comprises a liquid Nitrogen coolant or another cryogenic fluid.

3. The freezer of claim 1, comprising vent holes placed at predetermined locations on the payload bay.

4. The freezer of claim 1, comprising a separate compartment located between the payload bay and the outside environment with an insulation of between 2 and 4 inches thick.

5. The freezer of claim 1, wherein the controller is coupled to a thermocouple inside the payload bay, wherein the thermocouple measures temperature and when a setpoint is reached, the controller stops coolant flow through the evaporator coils using the one cryogenic valve.

6. The freezer of claim 5, wherein the controller performs PID control to maintain the setpoint within a predetermined limit.

7. The freezer of claim 1, wherein one of the cryogenic valves comprises a solenoid valve.

8. The freezer of claim 1, comprising heating pads or silicone rubber heaters located in an air flow path.

9. The freezer of claim 1, comprising a thermal barrier isolating thermal flow between the payload bay and a freezer door.

10. The freezer of claim 1, comprising a thermal barrier having a gap approximately ¼ inch wide and structurally reinforced with a non-metal material attached to both sides of the gap.

11. The freezer of claim 1, comprising a mechanical valve located in parallel with the one of the cryogenic valves valve to manually regulate the freezer temperature.

12. The freezer of claim 1, comprising an energy storage device to provide backup power to operate the controller and electronics.

13. The freezer of claim 1, comprising a safety valve.

14. The freezer of claim 13, comprising heating fins coupled to the valve and to keep the temperature of the valve warmer during pressure relief.

15. A system, comprising:
 a liquid Nitrogen inlet capable of convenient attachment to a customer's liquid Nitrogen supply;
 a cryogenic flow system that operates at a predetermined Nitrogen flow;
 a payload bay with removable shelves;
 a plurality of evaporators inside the payload bay;
 one or more cryogenic valves located at an exhaust port of the freezer;
 a fan and evaporator support structure with a multiplicity of holes that selectively direct the cooled airflow to provide even cooling throughout the payload bay;
 a thermal box immediately outside the evaporators and payload bay, that effectively thermally seals the payload bay from the outside environment, significantly reducing heat gain;

an electronic controller that maintains a setpoint for the payload bay, determined by the operator to be between approximately 20 degree C. and −150 degree C.;

a pneumatic latch that secures the freezer, and a pneumatic rubber seal that provides an airtight seal for the payload bay that is placed between a freezer door and the payload bay, the pneumatic latch and seal powered by the pressure derived from an exhaust gas;

an interactive Human Machine Interface (HMI), and a data logging unit with real time data plotted on the HMI and recording temperature and time; and a wireless transceiver to communicate real time data over the Internet.

16. A freezer, comprising:

a plurality of shelves in an insulated payload bay;

a plurality of evaporators coupled to the payload bay with a parallel array of coolant tubes in each evaporator, further comprising one or more cryogenic valves coupled to the coolant tubes;

a pump to force a cryogenic coolant flowing through the evaporators with a pressure of at least 90 psi to supply the coolant at each evaporator with at least 20 gallons per hour of coolant;

one or more cryogenic valves located at an exhaust port of the freezer;

a rubber pneumatic seal placed between a freezer door and the payload bay;

a pneumatic latch that secures the freezer door and the pneumatic rubber seal are powered by the pressure derived from an exhaust gas;

a plurality of fans to circulate cooled air in the payload bay;

a room heat exchanger valve controlling a flow of cryogen to a room heat exchanger, after the cryogen exits from the evaporators, a room fan that forces air through said room heat exchanger, where the air is cooled and delivered to a room, wherein the fan is controlled by a controller with a room thermocouple as a feedback loop.

* * * * *